(12) United States Patent
Haraguchi

(10) Patent No.: US 10,932,875 B2
(45) Date of Patent: Mar. 2, 2021

(54) MANIPULATOR, MEDICAL SYSTEM, AND MEDICAL SYSTEM CONTROL METHOD

(71) Applicant: OLYMPUS CORPORATION, Tokyo (JP)

(72) Inventor: Masafumi Haraguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 404 days.

(21) Appl. No.: 15/876,508

(22) Filed: Jan. 22, 2018

(65) Prior Publication Data
US 2018/0140168 A1 May 24, 2018

Related U.S. Application Data

(63) Continuation of application No. PCT/JP2016/071599, filed on Jul. 22, 2016.
(Continued)

(51) Int. Cl.
*A61B 34/37* (2016.01)
*A61B 34/35* (2016.01)
(Continued)

(52) U.S. Cl.
CPC .......... *A61B 34/37* (2016.02); *A61B 1/00006* (2013.01); *A61B 1/008* (2013.01);
(Continued)

(58) Field of Classification Search
CPC ..... A61B 1/00156; A61B 1/0016; A61B 1/31; A61B 1/0055; A61B 1/0008;
(Continued)

(56) References Cited

U.S. PATENT DOCUMENTS 5,820,545 A 10/1998 Arbter et al.
6,424,885 B1 7/2002 Niemeyer et al.
(Continued)

FOREIGN PATENT DOCUMENTS

CN 104582629 A 4/2015
EP 0 776 738 A2 6/1997
(Continued)

OTHER PUBLICATIONS

Office Action dated May 12, 2020 received in U.S. Appl. No. 15/872,032.
(Continued)

*Primary Examiner* — Alexandra L Newton
(74) *Attorney, Agent, or Firm* — Scully, Scott, Murphy & Presser, P.C.

(57) ABSTRACT

A medical system including a manipulator having a longitudinal portion with a proximal end and a distal end; a rotation driving unit connected to the longitudinal portion for rotating the proximal end; an uneven portion disposed on an outer circumference surface in the vicinity of the distal end and being along a helix; a bendable portion disposed at the distal end; a bending driving unit bending the bendable portion; a shape sensor unit detecting a bending amount and a bending direction of the bendable portion; a rotation angle sensor unit detecting a rotation angle and a rotation direction of the longitudinal portion; and a control unit controlling operations of the rotation driving unit and the bending driving unit, wherein the distal end and the uneven portion are rotatable about the longitudinal axis following the rotation of the proximal end when the proximal end is rotated by the rotation driving unit.

7 Claims, 9 Drawing Sheets

Related U.S. Application Data

(60) Provisional application No. 62/195,869, filed on Jul. 23, 2015.

(51) Int. Cl.

| | | |
|---|---|---|
| *A61B 34/00* | (2016.01) | |
| *A61B 1/00* | (2006.01) | |
| *A61B 1/005* | (2006.01) | |
| *A61B 1/01* | (2006.01) | |
| *A61B 1/008* | (2006.01) | |
| *A61B 1/018* | (2006.01) | |
| *A61B 1/05* | (2006.01) | |
| *A61B 34/30* | (2016.01) | |
| *A61B 90/00* | (2016.01) | |
| *B25J 9/16* | (2006.01) | |
| *A61B 90/30* | (2016.01) | |
| *A61B 17/00* | (2006.01) | |

(52) U.S. Cl.
CPC .......... *A61B 1/0016* (2013.01); *A61B 1/0055* (2013.01); *A61B 1/00133* (2013.01); *A61B 1/00149* (2013.01); *A61B 1/00193* (2013.01); *A61B 1/01* (2013.01); *A61B 1/018* (2013.01); *A61B 1/05* (2013.01); *A61B 34/30* (2016.02); *A61B 34/35* (2016.02); *A61B 34/70* (2016.02); *A61B 34/74* (2016.02); *A61B 90/37* (2016.02); *B25J 9/1633* (2013.01); *A61B 1/00039* (2013.01); *A61B 1/00045* (2013.01); *A61B 1/0057* (2013.01); *A61B 90/30* (2016.02); *A61B 90/36* (2016.02); *A61B 90/361* (2016.02); *A61B 2017/00367* (2013.01); *A61B 2034/301* (2016.02); *A61B 2034/303* (2016.02); *A61B 2034/306* (2016.02); *A61B 2090/061* (2016.02); *A61B 2090/064* (2016.02); *A61B 2090/065* (2016.02); *A61B 2090/306* (2016.02)

(58) Field of Classification Search
CPC ............ A61B 1/00147; A61B 1/00133; A61B 1/0051; A61M 25/0105; A61M 2025/006
See application file for complete search history.

(56) References Cited

U.S. PATENT DOCUMENTS

| 6,671,581 | B2 | 12/2003 | Niemeyer et al. | |
|---|---|---|---|---|
| 2002/0128552 | A1 | 9/2002 | Nowlin et al. | |
| 2003/0060927 | A1 | 3/2003 | Gerbi et al. | |
| 2005/0075739 | A1 | 4/2005 | Nishizawa | |
| 2007/0059989 | A1 | 3/2007 | Kura et al. | |
| 2007/0083098 | A1 | 4/2007 | Stern et al. | |
| 2008/0009675 | A1* | 1/2008 | Kura ................. | A61B 1/00156 600/137 |
| 2009/0209812 | A1* | 8/2009 | Omoto ............... | A61B 1/00158 600/110 |
| 2010/0016666 | A1 | 1/2010 | Hasegawa | |
| 2010/0030023 | A1 | 2/2010 | Yoshie | |
| 2010/0121145 | A1* | 5/2010 | Donhowe ........... | A61B 5/065 600/117 |
| 2010/0121151 | A1* | 5/2010 | Donhowe ........... | A61B 5/065 600/141 |
| 2010/0168763 | A1 | 7/2010 | Zhao et al. | |
| 2010/0274087 | A1 | 10/2010 | Diolaiti et al. | |
| 2010/0318100 | A1 | 12/2010 | Okamoto et al. | |
| 2011/0208000 | A1* | 8/2011 | Honda .............. | A61B 1/00154 600/118 |
| 2012/0059519 | A1 | 3/2012 | Kishi | |
| 2012/0108902 | A1* | 5/2012 | Frassica ........... | A61B 1/00094 600/114 |
| 2012/0209069 | A1 | 8/2012 | Popovic et al. | |
| 2013/0345719 | A1 | 12/2013 | Donhowe et al. | |
| 2014/0276951 | A1 | 9/2014 | Hourtash et al. | |

FOREIGN PATENT DOCUMENTS

| JP | H01221134 | A | 9/1989 |
|---|---|---|---|
| JP | H10113396 | A | 5/1998 |
| JP | 2002537884 | A | 11/2002 |
| JP | 2005103741 | A | 4/2005 |
| JP | 2007260431 | A | 10/2007 |
| JP | 2009195489 | A | 9/2009 |
| JP | 2010253162 | A | 11/2010 |
| JP | 2013049121 | A | 3/2013 |
| JP | 2015024026 | A | 2/2015 |
| JP | 2015511148 | A | 4/2015 |
| WO | 0051486 | A1 | 9/2000 |
| WO | 2005089630 | A1 | 9/2005 |
| WO | 2005110192 | A1 | 11/2005 |
| WO | 2006035566 | A1 | 4/2006 |
| WO | 2013116869 | A1 | 8/2013 |
| WO | 2014084408 | A1 | 6/2014 |
| WO | WO 2014/139023 | A1 | 9/2014 |
| WO | 2015/012242 | A1 | 1/2015 |

OTHER PUBLICATIONS

Office Action dated Apr. 29, 2020 received in U.S. Appl. No. 15/875,317.
Chinese Office Action dated Oct. 24, 2019 in Chinese Patent Application No. 201680042333.8.
Extended Supplementary European Search Report dated Feb. 21, 2019 in European Patent Application No. 16 82 7861.2.
Extended Supplementary European Search Report dated May 31, 2019 in European Patent Application No. 16827863.8.
International Search Report dated Oct. 11, 2016 issued in PCT/JP2016/071599.
International Search Report dated Oct. 18, 2016 issued in PCT/JP2016/071581.
International Search Report dated Oct. 18, 2016 issued in PCT/JP2016/071586.
Extended Supplementary European Search Report dated Mar. 20, 2019 in European Patent Application No. 16 82 7868.7.
Office Action dated Oct. 7, 2020 received in U.S. Appl. No. 15/872,032.
Office Action dated Oct. 19, 2020 received in U.S. Appl. No. 15/875,317.

* cited by examiner

MANIPULATOR, MEDICAL SYSTEM, AND MEDICAL SYSTEM CONTROL METHOD

This application is a continuation application based on a PCT International Application No. PCT/JP2016/071599, filed on Jul. 22, 2016, whose priority is claimed on U.S. Provisional Application No. 62/195,869, filed on Jul. 23, 2015. The contents of both the PCT International Application and the U.S. Provisional Application are incorporated herein by reference.

BACKGROUND OF THE INVENTION

Field of the Invention

The present invention relates to a manipulator, a medical system, and a medical system control method.

Description of Related Art

A manipulator such as an endoscope which is inserted into luminal organs such as the gastrointestinal tract and the like is well-known.

In Japanese Unexamined Patent Application, First Publication No. H10-113396, a propulsion apparatus configured to move an endoscope and a catheter or the like inside the luminal organs is disclosed. The propulsion apparatus disclosed in Japanese Unexamined Patent Application, First Publication No. H10-113396 includes a rotary member which is disposed at a distal end of an insertion portion of the endoscope such that the rotary member is rotatable with respect to the endoscope about a center line of the endoscope as a rotary axis. An outer circumference surface of the rotary member includes a rib which is formed to be inclined with respect to the rotary axis. The rotary member rotates with respect to the insertion portion and the rib formed in the rotary member functions as an impeller such that the propulsion apparatus disclosed in Japanese Unexamined Patent Application, First Publication No. H10-113396 can make the insertion portion to advance and retract along a direction of the rotary axis of the rotary member.

SUMMARY OF THE INVENTION

According to a first aspect of the present invention, a medical system includes a manipulator, wherein the manipulator includes a longitudinal portion configured to have a distal end and a proximal end, the longitudinal portion being inserted into a body cavity from the distal end; a rotation driving unit configured to rotate the proximal end about a longitudinal axis of the longitudinal portion as a rotary axis; an uneven portion disposed on an outer circumference surface in the vicinity of the distal end, the uneven portion being configured along a helix with the longitudinal axis as a helical axis or a straight line which is skew with respect to the longitudinal axis, a bendable portion disposed at the distal end, the bendable portion being operatable to bend; a bending driving unit configured to bend the bendable portion; a shape sensor unit configured to detect a bending amount and a bending direction of the bendable portion; a rotation angle sensor unit configured to detect a rotation angle and a rotation direction of the longitudinal portion with the longitudinal axis of the longitudinal portion as the rotary axis; and a control unit connected to the rotation driving unit, the bending driving unit, the shape sensor unit, and the rotation angle sensor unit, the control unit being configured to control operations of the rotation driving unit and the bending driving unit, wherein the distal end and the uneven portion are rotatable about the longitudinal axis following the rotation of the proximal end when the proximal end is rotated by the rotation driving unit, and wherein the control unit includes a shape-acquisition unit configured to acquire a shape of the bendable portion based on a detection by the shape sensor unit; a rotation driving instruction generation unit configured to generate a rotation driving instruction for rotating the longitudinal portion; a shape-correction instruction generation unit configured to calculate an operation amount of the bendable portion and generate a shape-correction instruction for correcting the shape of the bendable portion based on the shape of the bendable portion acquired by the shape-acquisition unit before the longitudinal portion rotates by a predetermined degree, in order to cause the bending direction and the bending amount of the bendable portion after the longitudinal portion rotates by the predetermined degree to coincide with that before the rotation of the longitudinal portion, and a driving signal generation unit configured to generate driving signals for operating the rotation driving unit and the bending driving unit based on the rotation driving instruction and the shape-correction instruction, and to output the driving signals to the rotation driving unit and the bending driving unit respectively.

According to a second aspect of the present invention, in the medical system according to the first aspect, the medical system may further include a trocar having a tubular portion that is insertable by the longitudinal portion, wherein the rotation angle sensor unit is disposed in the tubular portion.

According to a third aspect of the present invention, in the medical system according to the first aspect, the bendable portion may include two or more than two arms, and a joint having a universal joint configured to connect two of the arms.

According to a fourth aspect of the present invention, the medical system according to the first aspect may further include an imaging unit disposed at a distal end of the bendable portion, and the control unit may further include a feature-point setting unit configured to extract a feature point of a target object from an image acquired by the imaging unit and recognize the target object based on the feature point, and a position-aberration correction calculation unit configured to calculate the operation amount of the bendable portion based on the feature point in order to cause the imaging unit to be directed to the target object.

According to a fifth aspect of the present invention, in the medical system according to the fourth aspect, the control unit may further include a video-signal generation unit configured to perform an image processing of rotating the image about a predetermined rotation center in the image, wherein an absolute value of a rotation amount of the image is the same with the absolute value of the rotation amount of the longitudinal portion detected by the rotation angle sensor unit, and a rotation direction of the image is opposite to the rotation direction of the longitudinal portion.

According to a sixth aspect of the present invention, in the medical system according to the first aspect, the control unit may further include a torsional amount acquisition unit configured to acquire a difference between the rotation angle detected by the rotation angle sensor unit and the rotation angle of the distal end of the longitudinal portion, wherein the shape-correction instruction generation unit may generate the shape-correction instruction based on the difference acquired by the torsional amount acquisition unit in order to cause the bending direction and the bending amount of the bendable portion after the distal end of the longitudinal portion rotates by the predetermined degree to coincide with the bending direction and the bending amount of the bendable portion before the distal end of the longitudinal portion rotates by the predetermined degree, respectively.

According to a seventh aspect of the present invention, a medical system control method comprising a manipulator including a longitudinal portion configured to have a distal end and a proximal end, the longitudinal portion being inserted into a body cavity from the distal end; a rotation driving unit configured to rotate the proximal end about a longitudinal axis of the longitudinal portion as a rotary axis; an uneven portion disposed on an outer circumference surface in the vicinity of the distal end, the uneven portion being configured along a helix with the longitudinal axis as a helical axis or a straight line being skew with respect to the longitudinal axis; a bendable portion disposed at the distal end, the bendable portion being operatable to bend; a bending driving unit configured to bend the bendable portion; a shape sensor unit configured to detect a bending amount and a bending direction of the bendable portion; a rotation angle sensor unit configured to detect a rotation angle and a rotation direction of the longitudinal portion with the longitudinal axis of the longitudinal portion as the rotary axis; and a control unit connected to the rotation driving unit, the bending driving unit, the shape sensor unit, and the rotation angle sensor unit, the control unit being configured to control operations of the rotation driving unit and the bending driving unit, wherein the distal end of the longitudinal portion and the uneven portion are rotatable about the longitudinal axis following the rotation of the proximal end when the proximal end is rotated by the rotation driving unit, the medical system control method includes: a shape-acquisition step of acquiring a shape of the bendable portion based on a detection by the shape sensor unit; a rotation driving instruction generating step of generating a rotation driving instruction for rotating the longitudinal portion; a shape-correction instruction generating step of calculating an operation amount of the bendable portion and generating a shape-correction instruction for correcting the shape of the bendable portion based on the shape of the bendable portion acquired in the shape-acquisition step before the longitudinal portion rotates by a predetermined degree, in order to cause the bending direction and the bending amount of the bendable portion after the longitudinal portion rotates by the predetermined degree to coincide with that before the rotation of the longitudinal portion, and a driving signal generation step of generating driving signals for operating the rotation driving unit and the bending driving unit based on the rotation driving instruction and the shape-correction instruction, and outputting the driving signals to the rotation driving unit and the bending driving unit.

According to an eighth aspect of the present invention, in the medical system control method according to the seventh aspect, wherein the medical system may further include an imaging unit disposed at a distal end of the bendable portion, wherein the medical system control method may further include a feature-point setting step of extracting a feature point of a target object from an image acquired by the imaging unit and recognizing the target object based on the feature point, and a position-aberration correction calculation step of calculating the operation amount of the bendable portion based on the feature point in order to cause the imaging unit to be directed to the target object.

According to a ninth aspect of the present invention, the medical system control method according to the eighth aspect may further include a video-signal generation step of performing an image processing of rotating the image about a predetermined rotation center in the image, an absolute value of a rotation amount of the image being the same with the absolute value of the rotation amount of the longitudinal portion detected by the rotation angle sensor unit, and a rotation direction of the image being opposite to the rotation direction of the longitudinal portion.

According to a tenth aspect of the present invention, the medical system control method according to the seventh aspect may further include a torsional amount acquisition step of acquiring a difference between the rotation angle detected by the rotation angle sensor unit and the rotation angle of the distal end of the longitudinal portion, and the shape-correction instruction generating step may include a step of generating the shape-correction instruction based on the difference acquired in the torsional amount acquisition step in order to cause the bending direction and the bending amount of the bendable portion after the distal end of the longitudinal portion rotates by the predetermined degree to coincide with the bending direction and the bending amount of the bendable portion before the distal end of the longitudinal portion rotates by the predetermined degree, respectively.

DETAILED DESCRIPTION OF THE INVENTION

First Embodiment

Figure 1:
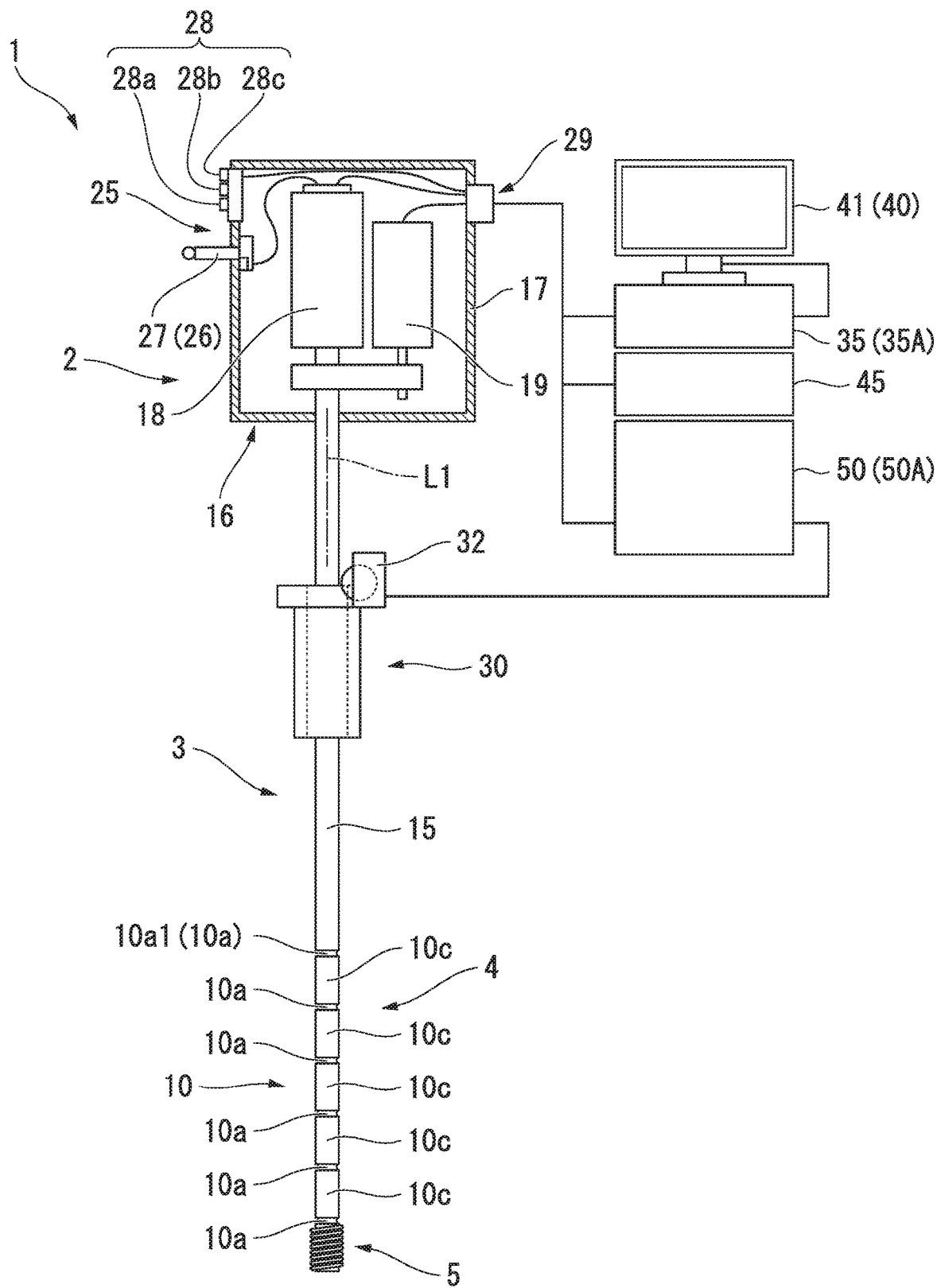
FIG. 1 is a schematic view showing a medical system including a manipulator according to a first embodiment of the present invention.
Figure 2:
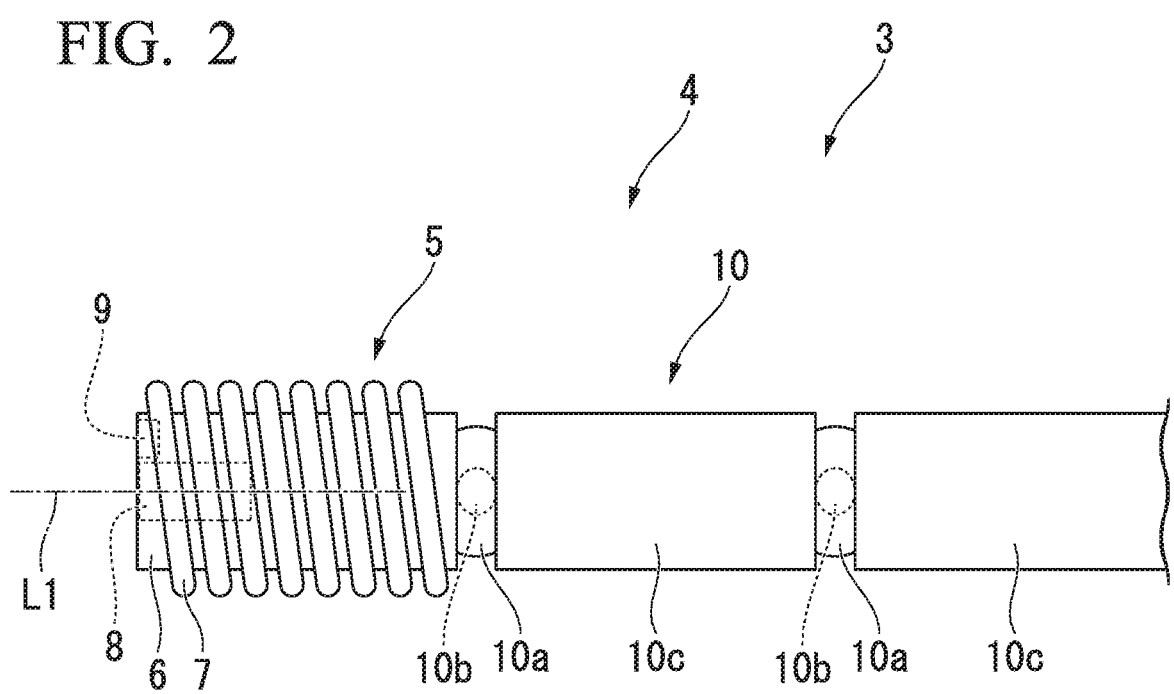
FIG. 2 is an enlarged view showing a distal end portion of the manipulator.
Figure 3:
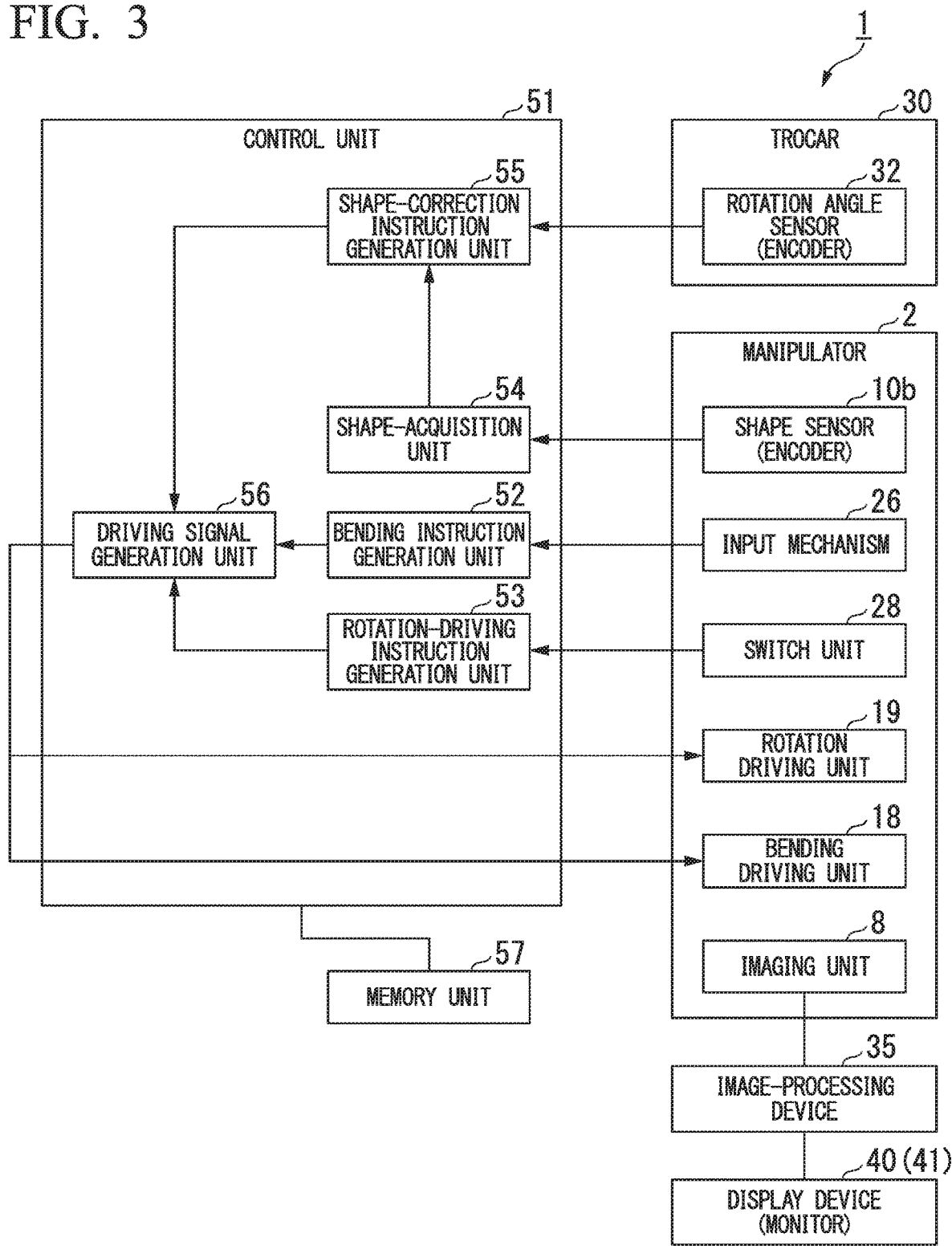
FIG. 3 is a block diagram showing essential parts of the medical system.
Figure 4:
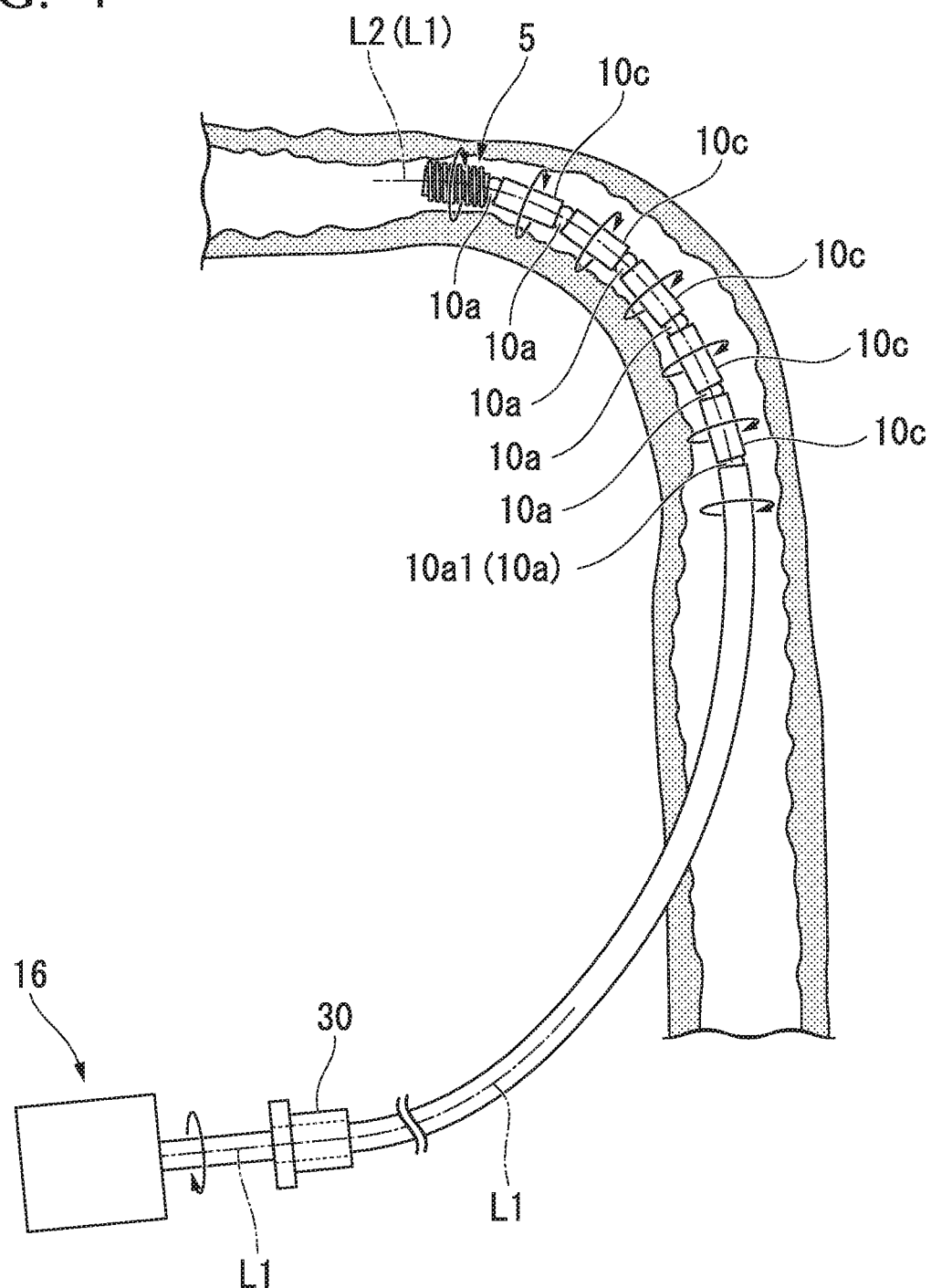
FIG. 4 is a view showing function of the medical system.

A first embodiment of the present invention will be described. FIG. 1 is a schematic view showing a medical system including a manipulator according to the present embodiment. FIG. 2 is an enlarged view showing a distal end portion of the manipulator. FIG. 3 is a block diagram showing essential parts of the medical system. FIG. 4 is a view showing function of the medical system.

As showing in FIG. 1, a medical system 1 according to the present embodiment includes a manipulator 2, a trocar 30, and a control device 50. The medical system 1 according to the present embodiment may also include an image-processing device 35, a display device 40, and a light source device 45 which are well-known.

The manipulator 2 is a device configured to be inserted into a body cavity and the gastrointestinal tract of a patient for observing organs and performing treatment on the organs. The manipulator 2 according to the present embodiment is connected to the control device 50, the image-processing device 35, the display device 40, and the light source device 45.

The manipulator 2 includes an insertion portion 3, a driving unit 16, an operation unit 25, and a connection unit 29.

As shown in FIG. 1 and FIG. 2, the insertion portion 3 is an elongated member that can be used in a state of being inserted inside the body cavity. The insertion portion 3 includes a distal end portion 4 and a longitudinal portion 15. The distal end portion 4 and the longitudinal portion 15 are insertable into the body cavity. The distal end portion 4 is disposed at a distal side of the longitudinal portion 15 along an insertion direction of the longitudinal portion 15 which is inserted into the body cavity. A channel used for inserting treatment tools and the like may be formed inside the insertion portion 3.

The distal end portion 4 includes a distal tubular portion 5, an imaging unit 8, an illumination unit 9, and a bendable portion 10.

As shown in FIG. 2, the distal tubular portion 5 includes a cylindrical main body portion 6 and an uneven portion 7 which is disposed on an outer circumference surface of the main body portion 6. An objective optical system of the imaging unit 8 and a window portion of the illumination unit 9 are disposed at a distal end of the main body portion 6. A proximal end of the main body portion 6 is connected to a distal end of the bendable portion 10.

The uneven portion 7 is formed as protruding outwardly in a radial direction of the main body portion 6 from the outer circumference surface of the main body portion 6. The uneven portion 7 is formed in a helical shape with a center line of the main body portion 6 (a straight line coaxial with a longitudinal axis L1 of the longitudinal portion 15) as an axis and the uneven portion 7 is extended on the outer circumference surface of the main body portion 6.

The imaging unit 8 is an end effector configured to acquire an image of an object as a treatment object. An optical axis of the imaging unit 8 extends more distally from the most distal end of the distal end portion 4. For example, the optical axis of the imaging unit 8 is coaxial with a center line of the distal tubular portion 5 (a straight line coaxial with the longitudinal axis L1 of the longitudinal portion 15). Accordingly, the imaging unit 8 according to the present embodiment has a field of view in a more distal region than the distal end portion 4 of the insertion portion 3. The imaging unit 8 can be configured by suitably adopting a configuration of an observation means of a conventional endoscope such as a CCD imaging device.

The imaging unit 8 outputs a signal of an acquired image (an image signal) to the image-processing device 35 via a connection unit 29 which will be described below.

The illumination unit 9 illuminates the field of view of the imaging unit 8 using light transmitted via an optical fiber (not shown) from the light source device 45. In a situation where the light source device 45 is not provided, the illumination unit 9 may include a light emitting element which emits illumination light forwardly from the distal end portion 4, such as an LED or the like.

The bendable portion 10 includes a plurality of joints 10a, each of the plurality of joints 10a having a rotary axis, a plurality of encoders (a shape sensor unit) 10b configured corresponding to the plurality of joints 10a respectively, and a plurality of arms 10c, each of the plurality of arms 10c connecting the two adjacent joints 10a.

The joints 10a are disposed at two ends of one of the plurality of the arms 10c. Accordingly, the bendable portion 10 is deformable to be bent at the rotary axis of the joint 10a. The joints 10a according to the present embodiment include universal joints which have axes orthogonal to each other respectively such that the two adjacent arms 10c swing around the joint 10a between the two adjacent arms 10c as a swing center.

The encoders 10b of the bendable portion 10 can detect operating amounts of the corresponding joints 10a. For example, by detecting bending angles at two axes (the two rotary axes of the joint 10a according to the present embodiment), wherein the two axes pass through the swing center of the joint 10a and the two axes are orthogonal to a center line of a relatively proximal arm 10c between the two adjacent arms 10c, the encoder 10b can detect a bending angle and a bending direction of the relatively distal arm 10c with respect to the relatively proximal arm 10c between the two adjacent arms 10c. In the bendable portion 10 according to the present embodiment, the plurality of joints 10a include a plurality of the encoders 10b for individually detecting the operating amounts of the corresponding joint 10a, respectively.

In the plurality of arms 10c according to the present embodiment, distances between the swing centers of the two joints 10a at the two ends of the arm 10c are equal.

The longitudinal portion 15 is a tubular member having flexibility and extending along a direction of the longitudinal axis L1. A distal end of the longitudinal portion 15 is connected to a proximal end of the bendable portion 10. A proximal end of the longitudinal portion 15 is connected to the driving unit 16. Angle wires (not shown) for connecting the bendable portion 10 and the driving unit 16 are inserted through the inside of the longitudinal portion 15.

As shown in FIG. 1, the driving unit 16 is connected to the proximal end of the longitudinal portion 15. The driving unit 16 includes a housing 17, a bending driving unit 18 connected to the longitudinal portion 15, and a rotation driving unit 19 configured to rotate the longitudinal portion 15 together with the bending driving unit 18.

The bending driving unit 18 is connected to the above described angle wires. The bending driving unit 18 includes a plurality of motors corresponding to each of the plurality of the joints 10a in order to generate forces for operating the plurality of joints 10a disposed at the bendable portion 10, and pulleys for transmitting the forces generated by the plurality of motors to the angle wires. The forces generated by the plurality of motors are transmitted to the bendable portion 10 via the angle wires.

The rotation driving unit 19 rotates the longitudinal portion 15 and the bending driving unit 18 with respect to the housing 17 about the longitudinal axis L1 of the longitudinal portion 15 as a rotary axis. The rotation driving unit 19 includes a motor to generate forces for rotating the longitudinal portion 15 and the bending driving unit 18.

The operation unit 25 includes an input mechanism 26 for inputting a bending direction and a bending amount of the bendable portion 10, and a switch unit 28 for inserting the insertion portion 3 into the body cavity and removing the insertion portion 3 from the body cavity.

The input mechanism 26 includes an input member 27 operated by an operator and an encoder, wherein the encoder is configured to output the bending direction of the bendable portion 10 to the control device 50 based on a direction in which the input member 27 is tilted from a predetermined neutral position, and the encoder is configured to output the bending amount of the bendable portion 10 to the control device 50 corresponding to an angle at which the input member 27 is tilted from the neutral position.

The switch unit 28 includes a first switch 28a for inserting the insertion portion 3 into the body cavity, a second switch 28b for removing the insertion portion 3 from the body cavity, and a third switch 28c for stopping the insertion and the removal of the insertion portion 3. The first switch 28a, the second switch 28b, and the third switch 28c are connected to the control device 50. The first switch 28a, the second switch 28b, and the third switch 28c output ON/OFF signals to the control device 50 according to an operation of the operator.

The connection unit 29 is connected to the driving unit 16. The connection unit 29 electrically connects the manipulator 2 to the image-processing device 35 and the control device 50.

The connection unit 29 includes a signal line for outputting a signal (an image signal) of an image acquired by the imaging unit 8 to the image-processing device 35, a signal line for outputting a driving signal from a control unit 51 described below to the driving unit 16 of the manipulator 2, and a signal line for outputting angle information detected by the encoder 10b of the manipulator 2 to the control unit 51 described below.

The connection unit 29 includes an optical fiber configured to transmit illumination light from the light source device 45 to the manipulator 2.

The trocar 30 includes a tubular portion 31 which is insertable into the longitudinal portion 15 of the manipulator and a rotation angle sensor unit 32 which is disposed inside the tubular portion 31.

The rotation angle sensor unit 32 includes a roller member which is supported by the tubular portion 31 such that the roller member can contact with an external surface of the longitudinal portion 15 and an encoder for detecting an operating amount of the roller member. The encoder of the rotation angle sensor unit 32 detects a rotation about a straight line parallel with a center line of the tubular portion 31 as a rotation axis among the rotations of the roller member. Accordingly, the rotation angle sensor unit 32 can detect the rotation of the longitudinal portion 15 when the longitudinal portion 15 inserted into the tubular portion 31 rotates about the center line of the tubular portion 31 as a rotation axis. The encoder of the rotation angle sensor unit 32 is connected to the control device 50.

The image-processing device 35 receives an input of the image signal output from the imaging unit 8. The image-processing device 35 generates a video signal based on the image signal output from the imaging unit 8 and outputs the video signal to the display device 40.

The display device 40 receives an input of the video signal output from the image-processing device 35. For example, the display device 40 includes an LCD monitor 41.

As shown in FIG. 1 and FIG. 3, the control device 50 includes a control unit 51 which controls the driving unit 16 of the manipulator 2, and a memory unit 57 which stores data generated at the control unit 51. Also, parameters relating to a shape of the bendable portion 10 of the manipulator 2 are stored in the memory unit 57. For example, the parameters include information relating to a characteristic joint coordinate system of the joint 10a and a length (a link length) of the arm 10c connecting the adjacent joints 10a.

As shown in FIG. 3, the control unit 51 is connected to the rotation driving unit 19, the bending driving unit 18, the encoder 10b configures the shape sensor unit of the bendable portion 10, and the rotation angle sensor unit 32.

The control unit 51 includes a bending instruction generation unit 52, a rotation-driving instruction generation unit 53, a shape-acquisition unit 54, a shape-correction instruction generation unit 55, and a driving signal generation unit 56.

The bending instruction generation unit 52 receives an input of a signal output from the input mechanism 26 of the operation unit 25. The bending instruction generation unit 52 calculates a bending direction and a bending amount of the bendable portion 10 based on information output by the encoder of the input mechanism 26. The bending instruction generation unit 52 according to the present embodiment sets a bending angle of each joint 10a based on the information output by the encoder of the input mechanism 26 such that the bending angles of the joints 10a included in the bendable portion 10 are equal to each other respectively. Accordingly, the bending instruction generation unit 52 according to the present embodiment sets the bending angle of each joint 10a such that the bendable portion 10 bends with a predetermined bending amount in a predetermined bending direction to cause a center line L2 of the bendable portion 10 to form a substantially circular shape. The bending instruction generation unit 52 outputs a bending instruction including information of the bending direction and the bending amount of the bendable portion 10 to the driving signal generation unit 56.

The rotation-driving instruction generation unit 53 generates a rotation-driving instruction including information relating to a rotation start and a rotation stop of a motor included in the rotation driving unit 19 and information of a rotation direction of the motor, based on the ON/OFF signals output by the first switch 28a, the second switch 28b, and the third switch 28c of the switch unit 28, and the rotation-driving instruction generation unit 53 outputs the rotation-driving instruction to the driving signal generation unit 56.

The shape-acquisition unit 54 receives an input of information output by the encoder 10b disposed in the bendable portion 10. The shape-acquisition unit 54 reads information of the joint coordinate system of each joint 10a in the bendable portion 10 from the memory unit 57, wherein the joint coordinate system is defined by specifying the swing center of each joint 10a of the bendable portion 10 as the origin point. The joint coordinate system of each joint 10a according to the present embodiment is a three-dimensional Cartesian coordinate system defined by specifying a longitudinal axis of the arm 10c (a rotation axis of the arm 10c) as the first axis X, wherein the arm 10c passes through the swing center of each joint 10a and the arm 10c is connected to the proximal end side of each joint.

The shape-acquisition unit 54 calculates orientation information of the joint 10a referred to an angle formed between the two arms 10c connected to the same one joint 10a and a bending direction of the arm 10c at the relatively distal side with respect to the arm 10c at the relatively proximal side. Further, the shape-acquisition unit 54 reads information of a length of the arm 10c connecting each joint 10a from the memory unit 57, and the shape-acquisition 54 specifies the joint coordinate system of the joint 10a (a proximal end joint 10a1) which is positioned most proximally in the bendable portion 10 as a reference coordinate system, and thus calculates the position and the orientation of each joint with respect to the reference coordinate system. The joint coordinate system of the proximal end joint 10a1 (in other words, the reference coordinate system of the bendable portion 10) is a three-dimensional Cartesian coordinate system defined by the longitudinal axis L1 of the longitudinal portion 15, and the two axes which pass the swing center of the proximal end joint 10a1 and are orthogonal to the longitudinal axis L1 of the longitudinal portion 15.

The shape-acquisition unit 54 associates the information including the position and the orientation of each joint in the reference coordinate system and a joint number for specifying the joint 10a to generate joint orientation information, and the shape-acquisition unit 54 outputs the joint orientation information to the shape-correction instruction generation unit 55.

The shape-correction instruction generation unit 55 receives an input of the joint orientation information generated by the shape-acquisition unit 54. Further, the shape-correction instruction generation unit 55 receives an input of information output by the encoder of the rotation angle sensor unit 32. Every time when a predetermined minute change of the angle output by the encoder of the rotation angle sensor unit 32 occurs, the shape-correction instruction generation unit 55 generates a shape-correction instruction for changing the orientation of the joint 10a included in the bendable portion 10 such that the position of every joint 10a in the reference coordinate system is constant before and after the change of the angle, and outputs the shape-correction instruction to the driving signal generation unit 56. The shape-correction instruction is an instruction for correcting the shape of the bendable portion by specifying the operating amount of the bendable portion 10 to secure that the bending direction and the bending amount of the bendable portion 10 after the longitudinal portion 15 rotates by a predetermined angle are the same with the bending direction and the bending amount of the bendable portion 10 before the longitudinal portion 15 rotates by the predetermined angle. The shape-correction instruction is unnecessary to be the instruction for specifying the operating amount of the bendable portion 10 to secure that the bending direction and the bending amount of the bendable portion 10 after the longitudinal portion 15 rotates by the predetermined angle are completely the same with that before the rotation. For example, the shape-correction instruction unit 55 can generate the shape-correction instruction to secure that the bending direction and the bending amount of the bendable portion 10 are in a predetermined threshold range (an allowable range) compared with that before the rotation.

The driving signal generation unit 56 receives an input of a rotation-driving instruction output by the rotation-driving instruction generation unit 53. The driving signal generation unit 56 generates a driving signal for causing the motor of the rotation driving unit 19 to forwardly rotate, reversely rotate, and stop based on the rotation-driving instruction, and the driving signal generation unit 56 outputs the driving signal to the rotation driving unit 19.

The driving signal generation unit 56 receives an input of the bending instruction output by the bending instruction generation unit 52. Further, the driving signal generation unit 56 receives an input of the shape-correction instruction output by the shape-correction instruction generation unit 55. The driving signal generation unit 56 generates a driving signal for operating the joint 10a based on the bending instruction and the shape-correction instruction and the driving signal generation unit 56 outputs the driving signal to the bending driving unit 18.

Effects of the medical system 1 according to the present embodiment will be described.

According to the present embodiment, when the operator operates the first switch 28a or the second switch 28b of the operation unit 25, the longitudinal portion 15 is controlled by the control device 50 to rotate with respect to the driving unit 16. In other words, according to the present embodiment, when an operation with respect to the first switch 28a or the second switch 28b is performed by the operator, as shown in FIG. 4, the longitudinal portion 15 rotates about the longitudinal axis L1 as the rotary axis inside the body cavity. Here, in the bendable portion 10 disposed at the distal end of the longitudinal portion 15, the orientation of each joint 10a is changed in accordance with the rotation angle of the longitudinal portion 15 by the shape-correction instruction generation unit 55 such that the position of each joint 10a in the reference coordinate system is maintained. Accordingly, when the longitudinal portion 15 is rotated about the center line of the longitudinal portion 15 as the rotary axis, the bendable portion 10 rotates about the center line of the bendable portion 10 as the rotary axis. All of the arms 10c included in the bendable portion 10 rotate about the center line of each arm 10c, respectively. The distal tubular portion 5 disposed at the distal end of the bendable portion 10 rotates integrally with the bendable portion 10 due to the self-rotation of the bendable portion 10. Accordingly, the distal tubular portion 5 rotates about the center line of the distal tubular portion 5 as the rotary axis in accordance with the rotation operation of the longitudinal portion 15 about the longitudinal axis L1 as the rotary axis.

The uneven portion 7 disposed on the outer circumference surface of the main body portion 6 of the distal tubular portion 5 (see FIG. 2) rotates about the center line (the straight line coaxial with the longitudinal axis L1 of the longitudinal portion 15) of the distal tubular portion 5 as the rotary axis in a state of being in contact with an inner surface of the luminal organs. By rotating the uneven portion 7 in a state in which the uneven portion 7 is caught by the inner surface of the luminal organs, the distal tubular portion 5 can advance and retract with respect to the luminal organs in a direction along the center line of the distal tubular portion 5. In other words, according to the present embodiment, a rotation force of the distal tubular portion 5 is transformed to a driving force of the distal tubular portion in the direction along the center line of the distal tubular portion, due to the uneven portion 7 disposed at the main body portion 6 of the distal tubular portion 5. An advancing direction and a retracing direction of the insertion portion 3 in the direction along the longitudinal axis (the longitudinal axis L1 of the longitudinal portion 15) of the insertion portion 3 can be switched when the operator uses the switch unit 28 to switch the rotation direction of the insertion portion 3.

When the insertion portion 3 is advanced and retracted by rotating the insertion portion 3, if necessary, the operator can use the operation unit 25 to change the bending direction and the bending amount of the bendable portion 10. In this situation, the control device 50 changes the orientation of each joint 10a in accordance with the rotation angle of the longitudinal portion 15 such that the new bending state of the bendable portion 10 changed by the operation unit 25 can be maintained. For example, during the period when the control device 50 performs automatic control of the bending direction and the bending amount of the bendable portion 10 in accordance with the rotation of the insertion portion 3, the control device 50 repeatedly receives the input from the operation unit 25 at several timings at a predetermined interval and controls the bending state of the bendable portion 10 in accordance with the input. Accordingly, the operator can operate the bendable portion 10 such that the distal end of the insertion portion 3 faces a desired direction as the advancing direction of the insertion portion 3 while advancing the insertion portion 3.

The longitudinal portion 15 connected to the proximal end of the bendable portion 10 is more flexible than the bendable portion 10 itself, thus the longitudinal portion 15 deforms following the curved shape of the luminal organs after the bendable portion 10 has passed the curved part of the luminal organs.

In the medical system 1 according to the present embodiment, the uneven portion 7 disposed at the distal end of the insertion portion 3 can be rotated by rotating the longitudinal portion 15 about the longitudinal axis L1 of the longitudinal portion 15 as the rotary axis. Accordingly, in the medical system 1 according to the present embodiment, a configuration exclusively used for rotating the uneven portion 7 such as a torque wire and the like is unnecessary and the insertion portion 3 can be configured with a small diameter.

In the medical system 1 according to the present embodiment, the orientation of each joint 10a is changed such that the bendable portion 10 performs the self-rotation about the center line L2 of the bendable portion 10 as the self-rotation center, thus the insertion portion 3 can be advanced and retracted inside the luminal organs while the bending state of the bendable portion 10 with respect to the luminal organs is maintained.

In the medical system 1 according to the present embodiment, the trocar 30 including the rotation angle sensor unit 32 configured to detect the rotation angle of the longitudinal portion 15 is provided, thus it is possible to insert the manipulator 2 into the body cavity of the patient using the trocar 30 and detect the rotation angle of the longitudinal portion 15 with respect to the patient by using the trocar 30. Accordingly, a positional relationship between the patient and the manipulator 2 can be detected with a high level of accuracy such that a positional aberration of the bendable portion 10 inside the body cavity of the patient can be suppressed.

Second Embodiment

Figure 5:
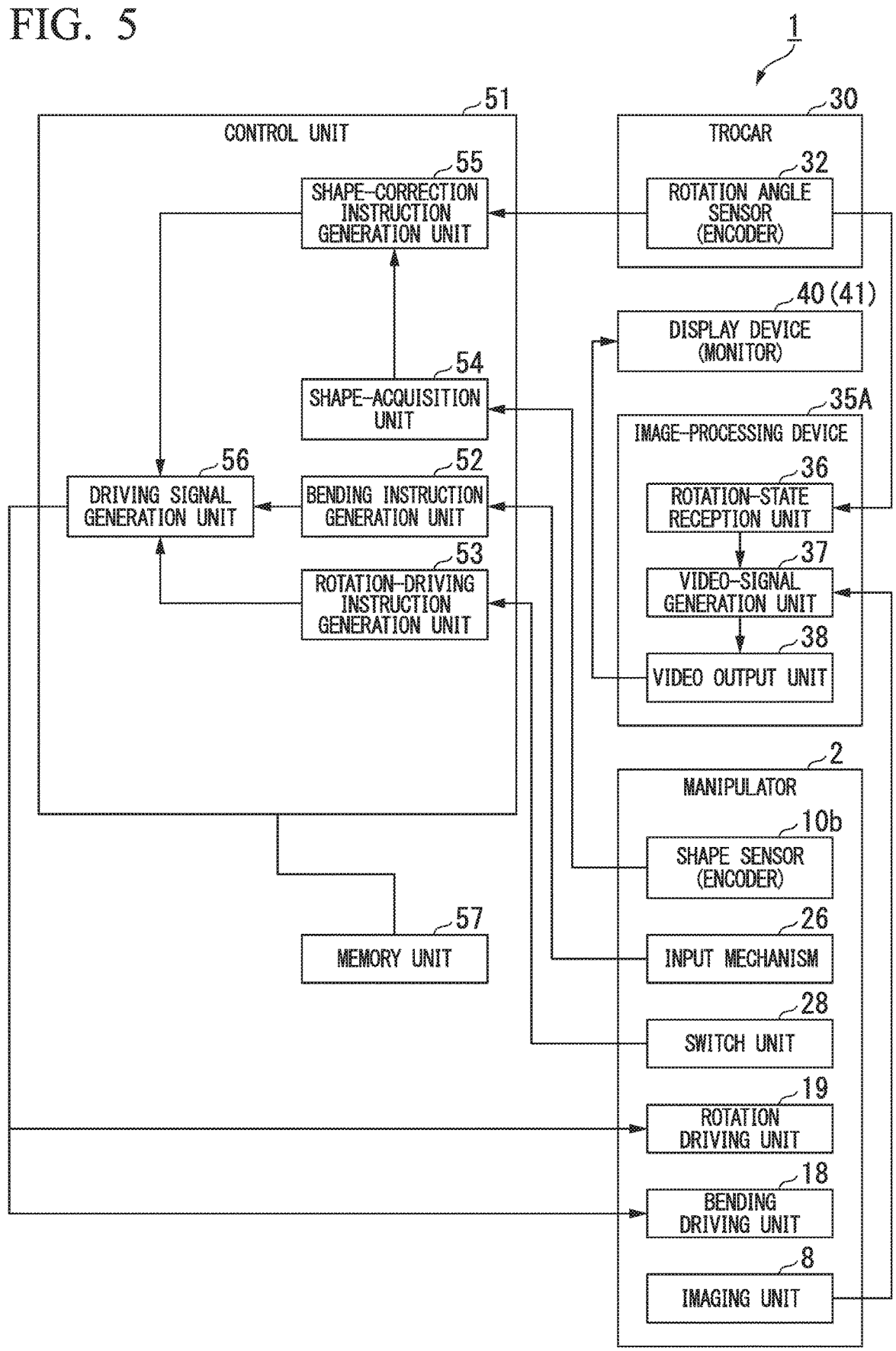
FIG. 5 is a block diagram showing a medical system according to a second embodiment of the present invention.
Figure 6:
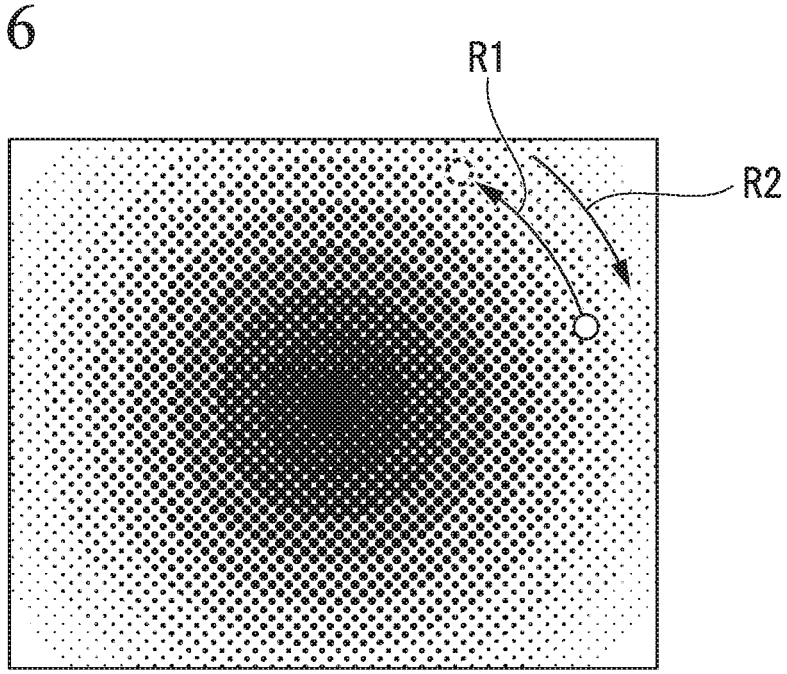
FIG. 6 is a schematic view showing an image displayed on a display device of the medical system.

A second embodiment of the present invention will be described. FIG. 5 is a block diagram showing a medical system according to the present embodiment. FIG. 6 is a schematic view showing an image displayed on a display device of the medical system.

A medical system 1 according to the present embodiment shown in FIG. 5 includes an image-processing device 35A having a different configuration with that of the image-processing device 35 according to the first embodiment.

The image-processing device 35A according to the present embodiment is connected to the control device 50. The image-processing device 35A includes a rotation-state reception unit 36, a video-signal generation unit 37, and a video output unit 38.

The rotation-state reception unit 36 acquires the rotation angle and the rotation direction of the longitudinal portion 15 which are detected by the rotation angle sensor unit 32 via the control device 50. The rotation-state reception unit 36 outputs the rotation-state information including the rotation angle and the rotation direction of the longitudinal portion 15 to the video-signal generation unit 37.

The video-signal generation unit 37 receives the image signal output by the imaging unit 8 and generates image data. The video-signal generation unit 37 receives an input of the information relating to the rotation angle and the rotation direction of the longitudinal portion 15 which are output by the rotation-state reception unit 36. The video-signal generation unit 37 associates a one-frame image in the image data with the rotation-state information output by the rotation-state reception unit 36. Further, the video-signal generation unit 37 rotates the image data about a center of the image as the rotary center such that a rotation direction of the rotated image data is opposite to that included in the rotation-state information and a magnitude (an absolute value of the bending amount) of the rotated image is the same with that included in the rotation-state information. The video-signal generation unit 37 generates a video signal based on the rotated image data and outputs the video signal to the video output unit 38. The video output unit 38 outputs the video signal to the monitor 41 of the display device 40.

Effects of the medical system 1 according to the present embodiment will be described.

An optical axis of the imaging unit 8 of the manipulator 2 is coaxial with the center line of the distal tubular portion 5. Accordingly, when the distal tubular portion 5 rotates, the imaging unit 8 rotates about the optical axis as the rotary axis (for example, shown as the reference sign R1 in FIG. 6). The video-signal generation unit 37 of the image-processing device 35A rotates the image in an opposite direction (for example, shown as the reference sign R2 in FIG. 6) with respect to the rotation direction of the imaging unit 8 rotating about the optical axis as the rotary axis and generates the video signal. Accordingly, in the image shown in the monitor 41 of the display device 40, effects due to the rotation of the imaging unit 8 are canceled such that vertical and horizontal relationships on the displayed image are maintained.

According to the present embodiment, in a situation when the insertion portion 3 is inserted into the luminal organs while observing the inside of the luminal organs, the image displayed by the display device 40 does not rotate despite of the rotation of the insertion portion 3 such that it is easy to observe the inside of the luminal organs.

Third Embodiment

Figure 7:
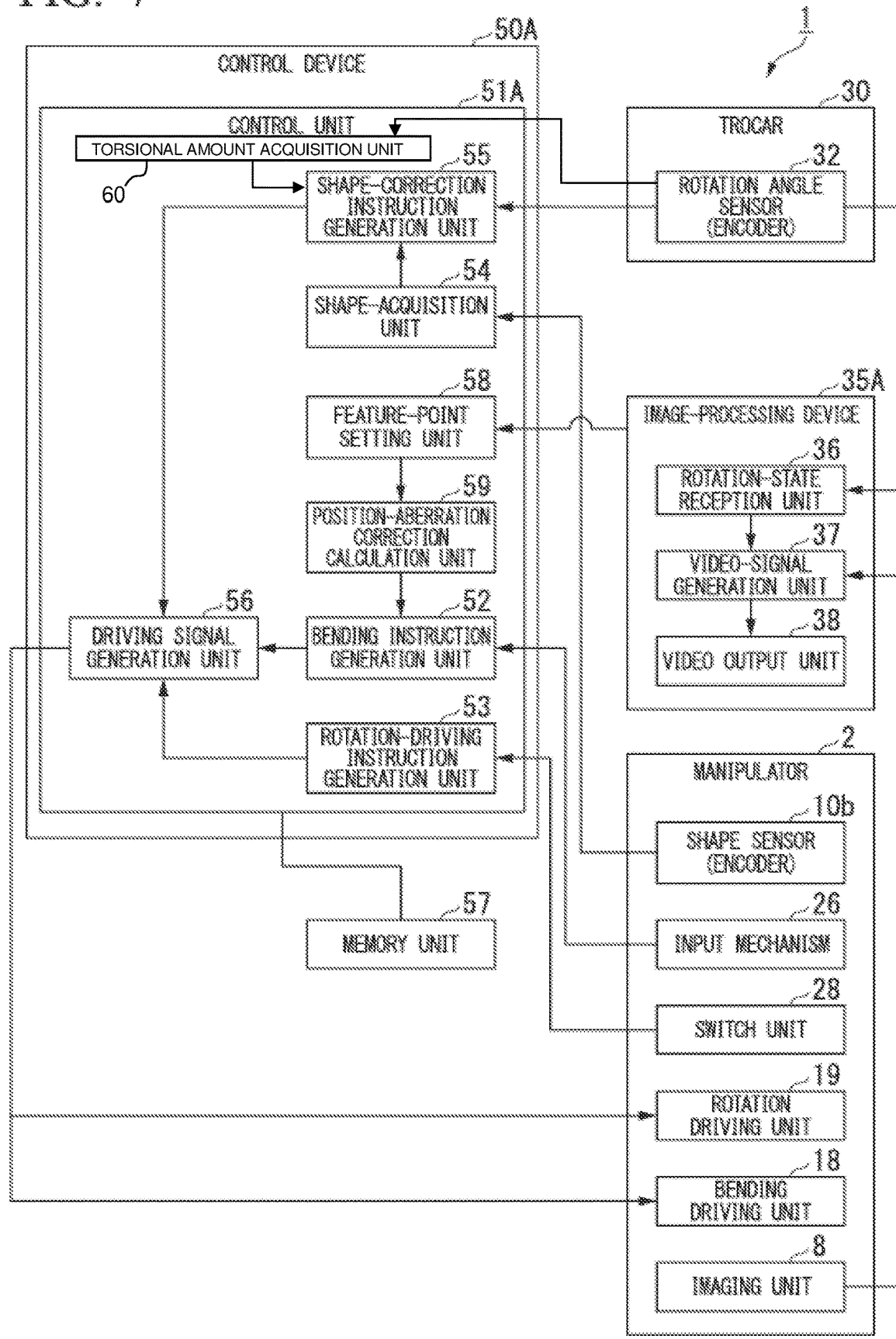
FIG. 7 is a block diagram showing a medical system according to a third embodiment of the present invention.
Figure 8:
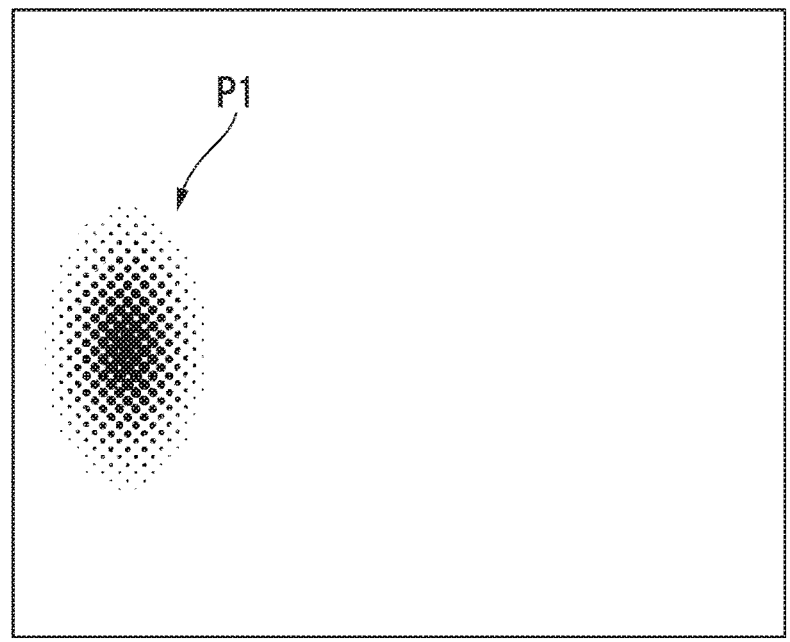
FIG. 8 is a schematic view showing an image displayed on a display unit of the medical system.
Figure 9:
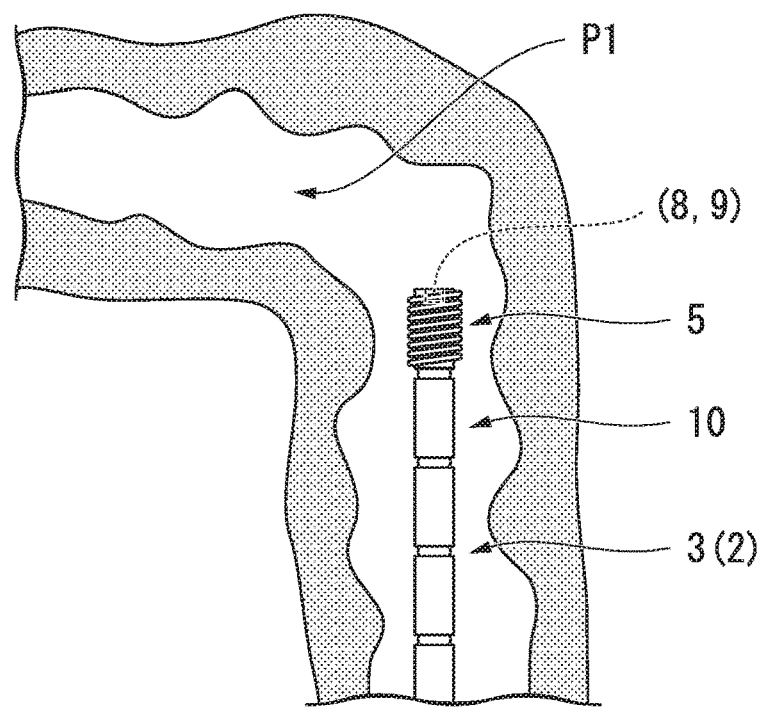
FIG. 9 is a schematic view showing a positional relationship of a manipulator in a luminal organ.
Figure 10:
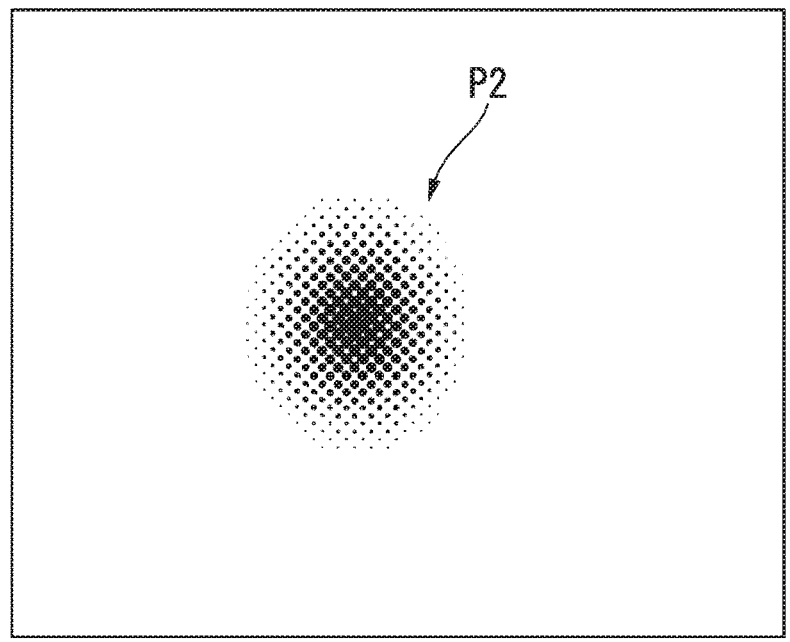
FIG. 10 is a schematic view showing an image displayed on the display unit of the medical system.
Figure 11:
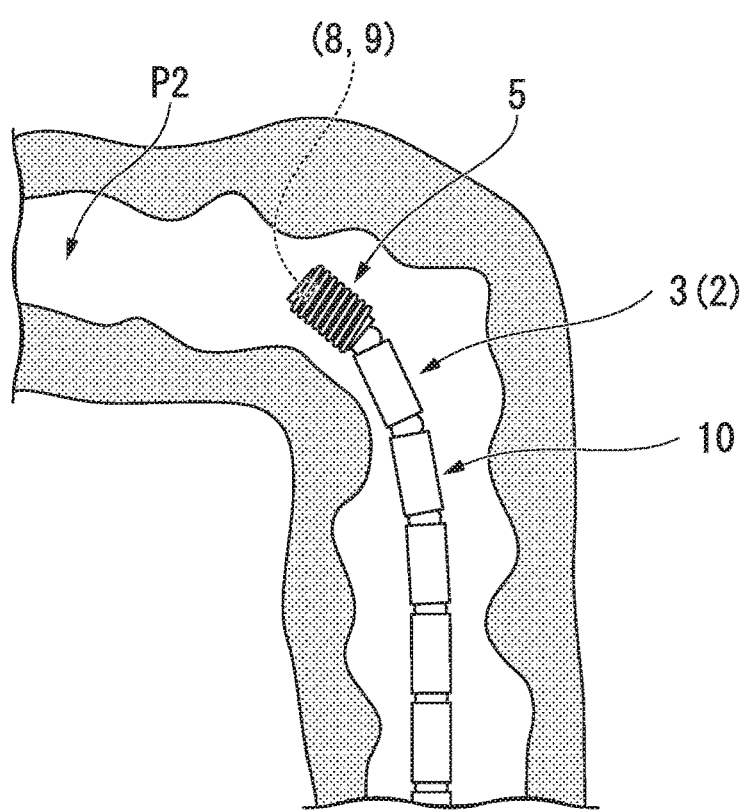
FIG. 11 is a schematic view showing a positional relationship of the manipulator in the luminal organ.

A third embodiment of the present invention will be described. FIG. 7 is a block diagram showing a medical system according to the present embodiment. FIG. 8 and FIG. 10 are schematic views showing images displayed on a display unit of the medical system, respectively. FIG. 9 and FIG. 11 are schematic views showing positional relationships of manipulators in luminal organs, respectively.

The medical system 1 according to the present embodiment shown in FIG. 1 and FIG. 7 includes a control device 50A which is different from the control device 50 disclosed in the first embodiment.

The medical system 1 according to the present embodiment includes the image-processing device 35A disclosed in the second embodiment and is configured to output the rotated image data to the control device.

The control device 50A according to the present embodiment controls operations of the rotation driving unit 19 and the bending driving unit 18 by setting a predetermined position included in the field of view of the imaging unit 8 as a movement target of the insertion portion 3, and as a result, the insertion portion 3 automatically moves toward the movement target.

The control device 50A includes a control unit 51A and the memory unit 57.

The control unit 51A, compared with the control unit 51 disclosed in the first embodiment, further includes a feature-point setting unit 58 and a position-aberration correction calculation unit 59.

The feature-point setting unit 58 receives an input of the image data output by the image-processing device 35, extracts feature points from the image included in the image data, and outputs the extracted feature points to the memory unit 57. The feature points extracted by the feature-point setting unit 58 according to the present embodiment are based on the characteristic shape and color of the target position when the insertion portion 3 is inserted into the body cavity. For example, as shown in FIG. 8 and FIG. 9, in a situation when the insertion portion 3 is inserted deeply into the luminal organs along the running direction of the luminal organs, the feature-point setting unit 58 outputs a dark region P1 in the field of view of the imaging unit 8, wherein a brightness of the dark region P1 is equal to or lower than a predetermined brightness, and thus the feature-point setting unit 58 can set the feature points of the position which is specified as the movement target of the insertion portion 3. In this case, the feature point (dark region P1) is a region apart from the illumination unit 9 in the field of view of the imaging unit 8 and the feature point corresponds to the deep position in the luminal organs.

The position-aberration correction calculation unit 59 receives the input of the image data output by the image-process device 35 and extracts the region corresponding to the feature point stored in the memory unit 57 from the image data. In a situation when the position of the feature point in the image data is apart from the center of the image with a distance equal to or larger than a predetermined distance, the position-aberration correction calculation unit 59 specifies and calculates the moving direction of the imaging unit 8 such that the center of the image moves toward the feature point. Further, the position-aberration correction calculation unit 59 calculates the bending direction of the bendable portion 10 for moving the imaging unit 8 along the specified direction. The position-aberration correction calculation unit 59 associates the bending direction and the bending amount for bending the bendable portion 10 with only a predetermined minute bending amount in the calculated bending portion and outputs them to the bending instruction generation unit 52.

According to the present embodiment, by adopting the feature-point setting unit 58 and the position-aberration correction calculation unit 59, the operation of the bendable portion 10 is controlled such that the distance between the center of the image and the feature point is decreased. The control by the feature-point setting unit 58 and the position-aberration correction calculation unit 59 is repeatedly performed and as a result, the center of the image coincides with the feature point.

Effects of the medical system 1 according to the present embodiment will be described.

When the medical system 1 according to the present embodiment is used, for example, in a situation when the dark region P1 in the image acquired by the imaging unit 8 is specified as the feature point, the position-aberration correction calculation unit 59 performs automatic control of the bending direction and the bending amount of the bendable portion 10 such that the distal end of the bendable portion 10 faces to the deep position of the luminal organs (see FIG. 9 and FIG. 11). In such a state, as the same with the first embodiment, when the distal tubular portion 5 rotates and the insertion portion 3 is pushed distally, the insertion portion 3 actively bends following the curved shape of the luminal organs and passes the curved part of the luminal organs.

Further, the feature-point setting unit 58 extracts a new dark region P2 (see FIG. 10) from the image acquired by the imaging unit 8 and specifies the dark region P2 as the feature point, and thus the position-aberration correction calculation unit 59 continues performing the automatic control of the bending direction and the bending amount of the bendable portion 10 such that the distal end of the bendable portion 10 faces to the deep position of the luminal organs. As a result, according to the present embodiment, the insertion portion 3 can be smoothly inserted into the luminal organs.

Preferred embodiments of the present invention have been described by referring to the figures, but the specific configurations are not limited to these embodiments thereof. Design changes of configurations can be made without departing from the spirit or scope of the present invention.

For example, the uneven portion disposed at the distal tubular portion is not limited to a continuously helical shape. Specifically, a plurality of the uneven portions may be disposed by a predetermined interval along a helix around the center line (a distal extension of the longitudinal axis L1 of the longitudinal portion) as a helical axis. The uneven portion may have a double helix shape around the center line of the distal tubular portion as the helical axis. Further, the uneven portion may have a linear portion extended to be inclined with respect to the outer circumference surface of the distal tubular portion such that the linear portion is skew with respect to the center line of the distal tubular portion.

The control unit may further include a torsional amount acquisition unit 60 for acquiring a difference between the rotation angle detected by the rotation angle sensor unit and the rotation angle of the distal end of the longitudinal portion. The torsional amount acquisition unit 60 estimates and outputs the rotation angle of the distal end of the longitudinal portion based on the rotation angle detected by the rotation angle sensor unit by using a parameter indicating a rotation delay amount of the distal end of the longitudinal portion when the proximal end of the longitudinal portion is rotated. At this time, the shape-correction instruction generation unit generates the shape-correction instruction such that the bending direction and the bending amount of the bendable portion are unchanged before and after the distal end of the longitudinal portion rotates by a predetermined degree, based on the difference acquired by the torsional amount acquisition unit 60.

The control unit may be configured to be able to acquire the position and the orientation of the insertion portion in the body cavity by using a well-known X-ray device. In such a situation, the position and the orientation of the longitudinal portion, and the bending direction and the bending amount of the bendable portion can be acquired based on the X-ray image.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. A medical system comprising a manipulator, wherein the manipulator comprises:
   a longitudinal portion configured to have a distal end that is insertable into a body cavity and a proximal end;
   an uneven portion disposed on an outer circumference surface in the vicinity of the distal end, the uneven portion being formed along a helix with the longitudinal axis as a helical axis or a straight line which is skew with respect to the longitudinal axis;

a bendable portion disposed at the distal end of the longitudinal portion, the bendable portion being configured to be operated to bend, wherein the bendable portion comprises:
   a plurality of joints, each of the plurality of joints having a rotary axis;
   a plurality of encoders corresponding to the plurality of joints respectively; and
   a plurality of arms, each of the plurality of arms connecting two adjacent joints of the plurality of joints;
a driver connected to the longitudinal portion, wherein the driver comprises:
   a bending driver comprising:
     a plurality of first motors, each of the plurality of first motors being configured to generate a first force for moving a corresponding one of the plurality of joints; and
     a plurality of pulleys configured to transmit the first force generated by the each of the plurality of first motors to the bendable portion through angle wires connecting the bendable portion and the driver to bend the bendable portion;
   a rotation driver comprising a second motor configured to generate a second force to rotate the proximal end of the longitudinal portion, wherein the distal end of the longitudinal portion and the uneven portion are configured to be rotated about the longitudinal axis following the rotation of the proximal end of the longitudinal portion; and
a plurality of first encoders corresponding to the plurality of joints, wherein the plurality of first encoders is configured to detect a bending amount and a bending direction of the bendable portion;
a trocar comprising:
   a tubular portion through which the longitudinal portion is insertable; and
   a rotation angle sensor disposed in the tubular portion and configured to detect a rotation angle and a rotation direction of the longitudinal portion with the longitudinal axis of the longitudinal portion as the rotary axis, wherein the rotation angle sensor comprises:
     a roller configured to be supported by the tubular portion to contact an external surface of the longitudinal portion; and
     a second encoder configured to detect an operating amount of the roller; and
a processor electrically connected to the rotation driver, the bending driver, the plurality of first encoders and the second encoder, wherein the processor is configured to:
   acquire a shape of the bendable portion based on a detection by the plurality of first encoders;
   generate a rotation driving instruction for rotating the longitudinal portion;
   calculate an operation amount of the bendable portion and generate a shape-correction instruction for correcting the shape of the bendable portion based on the shape of the bendable portion acquired before the longitudinal portion rotates by a predetermined degree, in order to cause the bending direction and the bending amount of the bendable portion after the longitudinal portion rotates by the predetermined degree to coincide with that before the rotation of the longitudinal portion;
   generate driving signals for operating the rotation driver and the bending driver based on the rotation driving instruction and the shape-correction instruction, and output the driving signals to the rotation driver and the bending driver; and
   acquire a torsional amount difference between the rotation angle detected by the rotation angle sensor and the rotation angle of the distal end of the longitudinal portion,
wherein the processor is configured to generate the shape-correction instruction based on the torsional amount difference so as to cause the bending direction and the bending amount of the bendable portion after the distal end of the longitudinal portion rotates by the predetermined degree to coincide with the bending direction and the bending amount of the bendable portion before the distal end of the longitudinal portion rotates by the predetermined degree, respectively.

2. The medical system according to claim 1,
wherein the plurality of joints of the bendable portion comprises a universal joint configured to connect two arms of the plurality of arms.

3. The medical system according to claim 1, further comprising: an image sensor disposed at a distal end of the bendable portion,
wherein the processor is further configured to:
   extract a feature point of a target object from an image acquired by the image sensor and recognize the target object based on the feature point; and
   calculate the operation amount of the bendable portion based on the feature point in order to cause the image sensor to be directed to the target object.

4. The medical system according to claim 3,
wherein the processor is further configured to perform an image processing to rotate the image about a predetermined rotation center in the image, an absolute value of a rotation amount of the image being the same with the absolute value of the rotation amount of the longitudinal portion detected by the rotation angle sensor, and a rotation direction of the image being opposite to the rotation direction of the longitudinal portion.

5. A medical system control method for controlling a manipulator,
wherein the manipulator comprises:
   a longitudinal portion configured to have a distal end that is insertable into a body cavity and a proximal end;
   an uneven portion disposed on an outer circumference surface in the vicinity of the distal end, the uneven portion being formed along a helix with the longitudinal axis as a helical axis or a straight line which is skew with respect to the longitudinal axis;
   a bendable portion disposed at the distal end of the longitudinal portion, the bendable portion being configured to be operated to bend, wherein the bendable portion comprises:
     a plurality of joints, each of the plurality of joints having a rotary axis;
     a plurality of encoders corresponding to the plurality of joints respectively; and
     a plurality of arms, each of the plurality of arms connecting two adjacent joints of the plurality of joints;
   a driver connected to the longitudinal portion, wherein the driver comprises:

a bending driver comprising:
   a plurality of first motors, each of the plurality of first motors being configured to generate a first force for moving a corresponding one of the plurality of joints; and
   a plurality of pulleys configured to transmit the first force generated by the each of the plurality of first motors to the bendable portion through angle wires connecting the bendable portion and the driver to bend the bendable portion;
a rotation driver comprising a second motor configured to generate a second force to rotate the proximal end of the longitudinal portion, wherein the distal end of the longitudinal portion and the uneven portion are configured to be rotated about the longitudinal axis following the rotation of the proximal end of the longitudinal portion; and
a plurality of first encoders corresponding to the plurality of joints, wherein the plurality of first encoders is configured to detect a bending amount and a bending direction of the bendable portion;
a trocar comprising:
   a tubular portion through which the longitudinal portion is insertable; and
   a rotation angle sensor disposed in the tubular portion and configured to detect a rotation angle and a rotation direction of the longitudinal portion with the longitudinal axis of the longitudinal portion as the rotary axis, wherein the rotation angle sensor comprises:
      a roller configured to be supported by the tubular portion to contact an external surface of the longitudinal portion; and
      a second encoder configured to detect an operating amount of the roller; and
wherein the medical system control method comprises:
   acquiring a shape of the bendable portion based on a detection by the plurality of first encoders;
   generating a rotation driving instruction for rotating the longitudinal portion;
   calculating an operation amount of the bendable portion and generating a shape-correction instruction for correcting the shape of the bendable portion based on the shape of the bendable portion acquired before the longitudinal portion rotates by a predetermined degree, in order to cause the bending direction and the bending amount of the bendable portion after the longitudinal portion rotates by the predetermined degree to coincide with that before the rotation of the longitudinal portion;
   generating driving signals for operating the rotation driver and the bending driver based on the rotation driving instruction and the shape-correction instruction, and outputting the driving signals to the rotation driver and the bending driver; and
   acquiring a torsional amount difference between the rotation angle detected by the rotation angle sensor and the rotation angle of the distal end of the longitudinal portion,
   wherein the shape-correction instruction is generated based on the torsional amount difference so as to cause the bending direction and the bending amount of the bendable portion after the distal end of the longitudinal portion rotates by the predetermined degree to coincide with the bending direction and the bending amount of the bendable portion before the distal end of the longitudinal portion rotates by the predetermined degree, respectively.

6. The medical system control method according to claim 5,
   wherein the medical system further comprises an image sensor disposed at a distal end of the bendable portion, and
   wherein the medical system control method further comprises:
      extracting a feature point of a target object from an image acquired by the image sensor and recognizing the target object based on the feature point; and
      calculating the operation amount of the bendable portion based on the feature point in order to cause the image sensor to be directed to the target object.

7. The medical system control method according to claim 6, further comprising performing an image processing to rotate the image about a predetermined rotation center in the image, an absolute value of a rotation amount of the image being the same with the absolute value of the rotation amount of the longitudinal portion detected by the rotation angle sensor unit, and a rotation direction of the image being opposite to the rotation direction of the longitudinal portion.

* * * * *